United States Patent [19]

Baumann et al.

[11] Patent Number: 4,644,069
[45] Date of Patent: Feb. 17, 1987

[54] PROCESS FOR THE PREPARATION OF DIMETHYLMALEIC ANHYDRIDE

[75] Inventors: Marcus Baumann; Werner Breitenstein, both of Basel, Switzerland

[73] Assignee: Ciba-Geigy Corporation, Ardsley, N.Y.

[21] Appl. No.: 762,755

[22] Filed: Aug. 6, 1985

[30] Foreign Application Priority Data

Aug. 15, 1984 [CH] Switzerland .................. 3909/84

[51] Int. Cl.[4] ......................................... C07D 307/60
[52] U.S. Cl. ................................................ 549/261
[58] Field of Search ....................................... 549/261

[56] References Cited

U.S. PATENT DOCUMENTS 3,818,050  6/1974  Baumann et al. ............... 549/261
3,833,619  9/1974  Baumann et al. ............... 549/261
4,480,106 10/1984  Breitenstein et al. ........... 549/253

FOREIGN PATENT DOCUMENTS 870681  6/1961  United Kingdom .

OTHER PUBLICATIONS

M. E. Baumann et al, Helv. Chim Acta 61, 2751 (1978).

Primary Examiner—Henry R. Jiles
Assistant Examiner—Bernard I. Dentz
Attorney, Agent, or Firm—Luther A. R. Hall

[57] ABSTRACT

The reaction of maleic acid, fumaric acid and/or maleic anhydride in the presence of N-acylated heterocyclic amidines and at elevated temperature affords dimethylmaleic anhydride in good yield. Catalytic amounts of the amidine employed are sufficient for said reaction.

14 Claims, No Drawings

PROCESS FOR THE PREPARATION OF DIMETHYLMALEIC ANHYDRIDE

The present invention relates to a process for the preparation of dimethylmaleic anhydride by reacting maleic acid, fumaric acid, maleic anhydride or mixtures thereof in the presence of N-acylated heterocyclic amidines or salts thereof and at elevated temperature.

Processes for the preparation of dimethylmaleic anhydride from 2 mol of maleic anhydride, maleic acid and/or fumaric acid are known from German published applications Nos. 2 233 862 and 2 233 889, said reaction being carried out at elevated temperature and in the presence of at least 1 mol of amidine containing a primary or secondary N atom. Good yields can only be obtained if the reaction mixture is subjected to acid hydrolysis. Furthermore, the large amount of amidine used is considered disadvantageous.

Accordingly, the present invention relates to a process for the preparation of dimethylmaleic anhydride by reacting 2 equivalents of maleic acid, fumaric acid and/or maleic anhydride in the presence of an amidine, an amidine salt or a mixture thereof and at a temperature of at least 90° C., in which process the amidine is of formula I and the amidine salt of formula II

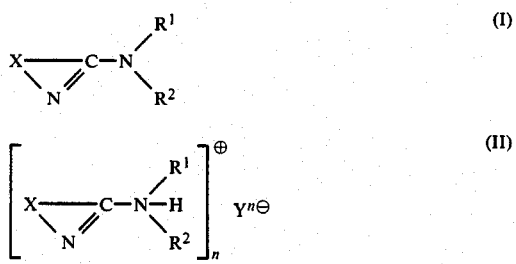

in which formulae $R^1$ is acyl and $R^2$ is a hydrogen atom, an aliphatic or aromatic hydrocarbon radical or acyl or $R^1$ and $R^2$ together are the diacyl radical of a 1,2-dicarboxylic acid, Y is the anion of an inorganic or organic protonic acid and n is an integer from 1 to 3, and X, together with the group

forms the radical of a substituted or unsubstituted 5- or 6-membered heterocyclic ring which may contain further hetero atoms.

In the process of the present invention, it is preferred to employ maleic acid, maleic anhydride or 1:1 mixtures (molar ratio) thereof.

Radicals of an unsubstituted or further substituted 5- or 6-membered heterocyclic ring which may contain further hetero atoms, which radicals are formed by X together with the group

are e.g. imidazolyl, pyrazolyl, triazolyl, thiazolyl, isothiazolyl, oxadiazolyl, thiadiazolyl, oxazolyl, pyridinyl, pyridazinyl, pyrimidinyl, pyrazinyl and triazinyl radicals.

If these radicals are further substituted, they may contain for example halogens such as fluorine, chlorine or bromine, phenyl groups, alkyl or alkoxy groups having 1 to 4 carbon atoms, amino groups, monoalkylamino or dialkylamino groups having 1 to 4 carbon atoms in each alkyl moiety, or hydroxyl groups, or they may be condensed with further monocyclic or heterocyclic rings. Preferred substituents are halogen, $C_1$-$C_4$-alkyl and $C_1$-$C_4$alkoxy. Examples of condensed 5- or 6-membered heterocyclic ring systems are: benzimidazole, benzothiazole, benzoxazole, pterin, purine, quinoline, isoquinoline, naphthyridine, phthalazine, cinnoline, quinazoline and quinoxaline.

Radicals or a 5- of 6-membered heterocyclic ring which are formed by X together with the group

are preferably not further substituted. The heterocyclic ring is preferably a 2-thiazolyl radical, especially the 2-pyridinyl radical.

The amidines of formula I are known or may be prepared in a manner known per se by acylating compounds of formula Ia

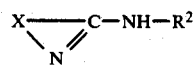

wherein X is as defined for formula I and $R^{2'}$ is a hydrogen atom or an aliphatic or aromatic hydrocarbon radical as defined for $R^2$. Examples of suitable starting amidines of formula Ia are: 2-aminoimidazole, 2-aminobenzimidazole, 3-aminopyrazole, 3-amino-5-methylpyrazole, 3-amino-4-bromo-5-methylpyrazole, 3-amino-1-phenylpyrazole, 3-amino-1,2,4-triazole, 3,5-diamino-1,2,4-triazole, 4-amino-1,2,3-triazole, 2-amino-1,3-thiazole, 3-aminoisothiazole, 2-amino-5-chlorothiazole, 2-amino-4-phenylthiazole, 2-aminobenzothiazole, 2-amino-6-bromobenzothiazole, 2-amino-4,6-dibromobenzothiazole, 3-amino-4-phenylfurazan, 3-amino-4-methylfurazan, 3-aminoisoxazole, 2-aminooxazole, 2-aminobenzoxazole, 2-aminopyridine, 2-amino-3-methylpyridine, 2-amino-4-methylpyridine, 2-amino-6-methylpyridine, 2-amino-5-bromopyridine, 2-amino-6-bromopyridine, 2-amino-5-chloropyridine, 2-amino-3,5-dibromopyridine, 2-amino-3,5-dichloropyridine, 2-amino-3-methylaminopyridine, 2,6-diaminopyridine, 2,3-diaminopyridine, 2-aminopyrazine, 2-aminopyrimidine, 6-amino-2-chloropyrimidine, 6-amino-2,4-dimethylpyrimidine, 2-amino-5-bromo-4,6-dimethylpyrimidine, 2-amino-6-chloropyrimidine, 2-amino-4,6-dichloropyrimidine, 6-amino-2,4-dichloropyrimidine, 2-amino-4,6-dimethylpyrimidine, 4,6-diaminopyrimidine, 6-amino-4-methylpyrimidine, 3-aminopyridazine, 2-amino-1,3,5-triazine, 2,4,6-triamino-1,3,5-triazine, 2-amino-4,6-dichloro-1,3,5-triazine, 2-amino-4,6-dimethyl-1,3,5-triazine, 4-amino-6-hydroxy-2-methyl-1,3,5-triazine, 2,4-diamino-6-methyl-1,3,5-triazine, 8-aminopurine, 2-aminopurine, 6-aminopurine (adenine), 2-amino-6-bromopurine, 2-amino-6-chloropurine, 6-amino-2,8-dichloropurine, 8-amino-2,6-dichloropurine, 6-amino-2-methylpurine, 2,8-diaminopurine, 6,8-diaminopurine, 7-methyl-2,6,8-triaminopurine, 1- aminoisoquinoline, 2-aminoquinoline, 2,4-diaminoquinoline, 2-amino-1,7-naphthyridine, 2-amino-1,5-naphthylidine, 2-amino-6,7-dimethyl-1,8-naphthyridine, 2-aminoquinoxaline, 2,3-diaminoquinoxaline, 4-aminoquinazoline.

If amidine salts of formula II are employed in the process of the present invention, then n is an integer from 1 to 3 and Y is preferably the anion of formic acid, acetic acid, propionic acid, hydrochloric acid, hydrobromic acid, sulfuric acid or phosphoric acid. However, Y is most preferably the anion of an aliphatic monocarboxylic acid having 2 to 4 carbon atoms, in particular acetic acid (n=1). These salts can be prepared in conventional manner by treating the amidine of formula I with the corresponding acid. This preparation can be effected direct in situ or the isolated salt can be used for the reaction.

$R^2$ is an aliphatic hydrocarbon radical is preferably branched or, in particular, linear $C_1$-$C_{12}$-alkyl, preferably $C_1$-$C_6$alkyl, or $C_5$-$C_7$-cycloalkyl and as an aromatic hydrocarbon radical is $C_6$-$C_{12}$aryl, $C_7$-$C_{16}$aralkyl, $C_7$-$C_{16}$alkaryl or $C_8$-$C_{16}$alkaralkyl. Examples are methyl, ethyl, n-propyl, isopropyl, n-butyl, isobutyl, tert-butyl, pentyl, hexyl, octyl, decyl, dodecyl, cyclopentyl, cyclohexyl, cycloheptyl, phenyl, naphthyl, benzyl, 2-phenylethyl, methylphenyl, ethylphenyl and methylbenzyl. $R^2$ is preferably a halogen atom.

$R^1$ and $R^2$ as acyl preferably contain 1 to 12 carbon atoms. The acyl radical may be of the formula $R^3CO$, wherein $R^3$ is linear or branched alkyl preferably containing 1 to 6 carbon atoms, cycloalkyl preferably containing 5 to 7 ring carbon atoms, aryl containing 6 to 12 carbon atoms or aralkyl containing 7 to 12 carbon atoms. Examples of acyl are formyl, acetyl, propionyl and benzoyl, with acetyl and propionyl being particularly preferred.

If $R^1$ and $R^2$ together are the diacyl radical of a 1,2-dicarboxylic acid, said radical, together with the N atom to which $R^1$ and $R^2$ are attached, forms a 5-membered imide ring. The diacyl radical may for example be substituted by $C_1$-$C_{12}$alkyl, halogen, preferably chlorine, or by cyano or phenyl and may correspond to the formula —CO—$R^4$—CO—, wherein $R^4$ is a divalent aliphatic or aromatic hydrocarbon radical to which the two carbonyl groups are attached in the 1,2-position. Examples of suitable diacyl radicals are 1,2-cyclohexylene, 1,2-cyclopentylene, ethylene, ethenylene and 1,2-phenylene. Examples of 1,2-dicarboxylic acids from which the diacyl radical is derived are 1,2-cyclopentanedicarboxylic and 1,2-cyclohexanedicarboxylic acid, succinic acid, alkylated succinic acids such as methylsuccinic, dimethylsuccinic, ethylsuccinic, propylsuccinic, isopropylsuccinic, butylsuccinic, pentylsuccinic, hexylsuccinic, octylsuccinic, decylsuccinic, dodecylsuccinic, phenylsuccinic or diphenylsuccinic acid, maleic acids such as maleic, methylmaleic, dimethylmaleic, ethylmaleic, propylmaleic, phenylmaleic, diphenylmaleic, cyanomaleic, 1-phenyl-2-methylmaleic and 1-methyl-2-cyanomaleic acid, phthalic acid, chlorophthalic acid, dichlorophthalic acid, tetrachlorophthalic acid or tetrabromophthalic acid. Most preferably, $R^1$ and $R^2$ together as diacyl radical are derived from phthalic acids, maleic acids or succinic acids.

The reaction of the present invention may be carried out in an organic solvent which is inert to the reactants. Examples of such solvents are unsubstituted or chlorinated aromatic hydrocarbons, e.g. benzene, toluene, xylenes, chlorobenzene or dichlorobenzenes, dialkyl sulfoxides, e.g. dimethyl sulfoxide, methyl cellosolve, hexamethylphosphoric triamide, N,N-dialkylamides of a lower monocarboxylic acid, e.g. dimethylformamide or dimethylacetamide, or lower dialkyl esters of carbonic acid, e.g. dimethyl carbonate or diethyl carbonate. Mixtures of such solvents may also be employed. If the amidine salt of the general formula II is prepared direct in situ, the acid used, e.g. an aliphatic $C_2$-$C_4$carboxylic acid, in particular acetic acid, may also be employed as solvent.

In accordance with a preferred embodiment, the reaction of the invention is carried out without addition of a solvent or, in particular, in anhydrous acetic acid.

The reaction temperature is preferably in the range from 90° to 200° C., most preferably from 110° to 180°0 C. The reaction may, if appropriate, be carried out under pressure.

A buffer compound, e.g. an alkali metal acetate such a sodium acetate, may also be added to the reaction mixture. If maleic anhydride is employed alone, it is convenient to add water, advantageously in an amount of 0.5 to 20% by weight, based on the amount of maleic anhydride employed.

The compounds of formulae I and II may be employed in amounts of up to at least 1 mol per 2 mol of maleic acid, fumaric acid and/or maleic anhydride. Surprisingly, it has been found that also the use of catalytic amounts of amidine of formula I or amidine salt of formula II is sufficient and that also when employing preferably 1 to 20 mol%, especially 1 to 10 mol% and, most preferably, 5 to 10 mol%, based on the reactants, the reaction affords high yields. The use of catalytic amounts is therefore preferred.

The isolation and purification of the reaction product are effected by conventional methods, e.g. distillation, steam distillation, extraction or crystallisation. It is a particular advantage of the process of the present invention that the reaction product can be isolated direct, without having to effect acid hydrolysis, so that high yields can be obtained. In this process, the amidine compounds can be recovered in quantitative yield.

Dimethylmaleic anhydride is a valuable intermediate for the preparation of light-sensitive polymers containing dimethylmaleic imidyl groups (q.v. German published application No. 2 626 769).

The invention is illustrated in more detail by the following Examples. Percentages are by weight.

EXAMPLE 1

116 g (1.0 mol) of maleic acid and 20.2 g (0.1 mol) of N-(pyrid-2-yl)-3,4-dimethylmaleinimide are boiled under reflux for 48 hours in 300 ml of glacial acetic acid. The residue is then steam distilled. The distillate is filtered and the filtrate is dried, affording 42.8 g (48%) of dimethylmaleic anhydride with a melting point of 91°-93° C. By extracting the residual aqueous phase with ether, a further 7.89 g (12.3%) of dimethylmaleic anhydride are isolated.

EXAMPLE 2

98.0 g (1.0 mol) of maleic anhydride are added in portions over 1 hour to a boiling solution of 20.2 g (0.1 mol) of N-(pyrid-2-yl)-3,4-dimethylmaleinimide and 9 ml (0.5 mol) of water in 400 ml of glacial acetic acid. The mixture is subsequently boiled under reflux for 22 hours. Working up as indicated in Example 1 affords 52.4 g (63%) of dimethylmaleic anhydride with a melting point of 92°-93° C.

EXAMPLE 3

A solution of 98 g (1.0 mol) of maleic anhydride in 300 ml of glacial acetic acid is added dropwise over 20 minutes to a boiling solution of 20.2 g (0.1 mol) of N-(pyrid-2-yl)-3,4-dimethylmaleinimide in 100 ml of glacial acetic acid. Subsequently, a solution of 9 ml (0.5 mol) of water in 50 ml of glacial acetic acid is added dropwise over 1½ hours and the mixture is boiled further for 20 hours. Working up as indicated in Example 1 affords 50.8 g (60.6%) of dimethylmaleic anhydride with a melting point of 91°–93° C.

EXAMPLE 4

A solution of 58.0 g (0.5 mol) of maleic acid, 49.0 g (0.5 mol) of maleic anhydride and 20.2 g (0.1 mol) of N-(pyrid-2-yl)-3,4-dimethylmaleinimide in 300 ml of glacial acetic acid is boiled under reflux for 6 hours. The glacial acetic acid is removed and the residue is then heated for 15 minutes to 150° C. After subsequent steam distillation of the residue, the resultant dimethylmaleic anhydride is isolated as indicated in Example 1. Yield: 37.1 g (39%).

EXAMPLES 5–14

A solution of 58 g (0.5 mol) of maleic acid, 49 g (0.5 mol) of maleic anhydride and the amidine or amidine salt are dissolved in 300 ml of glacial acetic acid and the mixture is heated under reflux for 48 hours. The glacial acetic acid is removed, the residue is then steam distilled and the resultant dimethylmaleic anhydride (DMA) is isolated in accordance with Example 1. Further details are given in the following Table.

| Example | Amidine or amidine salt | Amount (mol %) | Yield DMA (Percentage by weight) |
|---|---|---|---|
| 5 | [structure] | 10 | 18.7 |
| 6 | [structure] | 10 | 22.8 |
| 7 | [structure] | 10 | 49 |
| 8 | [structure] | 10 | 46.7 |
| 9 | [structure] | 50 (Test 1) | 8.7 |
|   |   | 50 (Test 2) | 15.0 |
| 10 | [structure] | 10 | 33 |
| 11 | [structure] | 50 (Test 1) | 7.3 |
|   |   | 50 (Test 2) | 30.5 |
| 12 | [structure] | 10 | 14.6 |
| 13 | [structure] | 10 | 9.8 |
| 14 | [structure] | 10 | 23.8 |

What is claimed is:

1. A process for the preparation of dimethylmaleic anhydride by reacting 2 equivalents of maleic acid, fumaric acid and/or maleic anhydride in the presence of an amidine, an amidine salt or a mixture thereof and at a temperature of at least 90° C., in which process the amidine is of formula I and the amidine salt of formula II

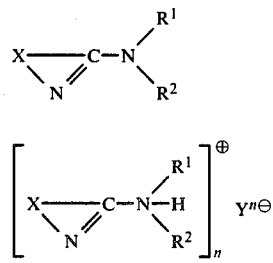

in which formulae $R^1$ is acyl and $R^2$ is a hydrogen atom, an aliphatic or aromatic hydrocarbon radical or acyl or $R^1$ and $R^2$ together are the diacyl radical of a 1,2-dicarboxylic acid, Y is the anion of an inorganic or organic protonic acid and n is an integer from 1 to 3, and X, together with the group

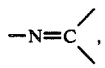

forms the radical of a substituted or unsubstituted 5- or 6-membered heterocyclic ring which may contain further hetero atoms.

2. A process according to claim 1, wherein the reaction is carried out in the presence of an inert solvent.

3. A process according to claim 2, wherein the solvent is an aliphatic carboxylic acid having 2 to 4 carbon atoms.

4. A process according to claim 3 wherein the solvent is acetic acid.

5. A process according to claim 1, which is carried out in the temperature range from 90° to 200° C.

6. A process according to claim 1, wherein 0.5 to 20% by weight of water, based on the amount of maleic anhydride, is added if said maleic anhydride is employed alone.

7. A process according to claim 1, wherein the heterocyclic ring is a 2-pyridyl radical or a 2-thiazolyl radical.

8. A process according to claim 1, wherein $R^2$ is an aliphatic hydrocarbon radical is $C_1$-$C_{12}$alkyl or $C_5$-$C_7$-cycloalkyl and as an aromatic hydrocarbon radical is $C_6$-$C_{12}$aryl, $C_7$-$C_{16}$aralkyl, $C_7$-$C_{16}$-alkaryl or $C_8$-$C_{16}$alkaralkyl.

9. A process according to claim 1, wherein $R^1$ and $R^2$ as acyl are acetyl or propionyl.

10. A process according to claim 1, wherein $R^1$ and $R^2$ together as diacyl radical are derived from a phthalic acid, a maleic acid or a succinic acid.

11. A process according to claim 1, wherein Y is the anion of an aliphatic monocarboxylic acid having 2 to 4 carbon atoms.

12. A process according to claim 11 wherein the anion Y is acetate.

13. A process according to claim 1, wherein the amidine of formula I or the amidine salt of formula II is employed in a catalytic amount of 1 to 20 mol%, based on the amount of maleic acid, fumaric acid and/or maleic anhydride.

14. A process according to claim 1, which comprises the use of maleic acid, maleic anhydride or a 1:1 mixture thereof.

* * * * *